United States Patent
Kaack et al.

(10) Patent No.: US 7,453,562 B1
(45) Date of Patent: Nov. 18, 2008

(54) ELLIPSOMETRY MEASUREMENT AND ANALYSIS

(75) Inventors: Torsten R. Kaack, Los Altos, CA (US); Shankar Krishnan, Santa Clara, CA (US); Fabio A. Faccini, San Jose, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 11/863,334

(22) Filed: Sep. 28, 2007

Related U.S. Application Data

(60) Provisional application No. 60/970,294, filed on Sep. 6, 2007.

(51) Int. Cl.
*G01N 21/00* (2006.01)
(52) U.S. Cl. .................................. 356/237.2
(58) Field of Classification Search ............... 356/237.1
See application file for complete search history.

(56) References Cited

U.S. PATENT DOCUMENTS

2006/0197945 A1* 9/2006 Tiemeyer et al. ......... 356/237.2
2006/0256326 A1* 11/2006 Bills et al. ............... 356/237.2

* cited by examiner

*Primary Examiner*—Roy M Punnoose
(74) *Attorney, Agent, or Firm*—Luedeka, Neely & Graham, P.C.

(57) ABSTRACT

A method of performing a measurement of properties of a sample, by directing a first beam of light at the sample, where a combination of the wavelength, energy, and length of time is sufficient to cause temporary damage to the sample. The first beam is reflected from the sample. The properties of the reflected beam are sensed to create a signal. A length of time is waited, sufficient for the damage to substantially heal, before a second beam of light is directed at the sample, where a combination of the wavelength, energy, and length of time is sufficient to cause temporary damage to the sample. The second beam is reflected from the sample. The properties of the reflected beam are sensed to create a signal. The first and second electrical signals are analyzed to determine the properties of the sample.

20 Claims, 2 Drawing Sheets

ELLIPSOMETRY MEASUREMENT AND ANALYSIS

This application claims all priorities and other benefits of prior pending U.S. provisional application 60/970,294, filed 2007 Sep. 6.

FIELD

This invention relates to the field of integrated circuit fabrication. More particularly, this invention relates to ellipsometric measurement and analysis of the properties of the materials and structures used in the fabrication of integrated circuits.

BACKGROUND

Integrated circuits are often formed on substrates, such as substrates of semiconducting material. Such substrates can hold as few as one or many as thousands of the integrated circuits. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

Integrated circuits are subjected to many different tests and analyses during the fabrication cycle, to determine whether the materials and structures of the integrated circuits are formed correctly. Such tests typically include ellipsometric or reflectometric analysis of the properties of various layers.

In general, any broad band ellipsometric measurement that extends into the deep ultraviolet or vacuum ultraviolet region is achieved by means of two or more light sources. Each light source provides a specific and limited wavelength range according to the nature and physics of the emission phenomenon, which is usually confined in an assembly such as a lamp. Two or more lamps are required—a separate lamp for each desired wavelength range—in order to obtain the desired signal to noise ratio in the measurement system. In a generic broad-band ellipsometer, the spectrum needed for measurement purposes is collected using all of the required lamps as light sources of the system. These lamps can be used individually, with each having its own specific optical path, or they can be combined in the same optical path. In order to perform a broad-band measurement, the system is engineered to collect measurement signals that come back from each light source in a serial mode, thus using the wavelength range of each lamp once per acquisition cycle. This is generally referred to as a combined measurement.

Specific applications, measurement sequences, or test conditions for ellipsometry may require a higher signal-to-noise ratio than is provided by the configurations generally described above. To achieve a higher signal to noise ratio it is often necessary to increase the integration time of the signal. For a rotating polarizer ellipsometer, this is referred to as an increased number of scans.

When a higher number of scans are required in a combined measurement, the system is used to independently and sequentially collect each wavelength portion of the signal, each with a specific number of scans, prior to moving to the next signal acquisition. The measurement result is provided as a combined regression of the multiple wavelength range signals.

Unfortunately, the deep ultraviolet and vacuum ultraviolet portions of electromagnetic spectrum are highly energetic, and thus interfere with the atomic or molecular structure of the sample. As a result, there is interaction between the measurement signal and the sample, both at the surface and also within the body of the sample. The main phenomenon at the surface is commonly understood to be the interaction of the light with contaminants at thermodynamic equilibrium. The interaction in the body is thought to be driven by atomic absorption of the light photons. As a result, combining vacuum ultraviolet measurements with higher numbers of scans causes higher magnitude effects, which condition is aggravated while performing repeated measurement acquisitions at the same physical location. This results in the measurements showing a trend due to the change resulting from repeated vacuum ultraviolet or deep ultraviolet exposure.

What is needed, therefore, is a system that overcomes problems such as those described above, at least in part.

SUMMARY

The above and other needs are met by a method of performing a measurement of properties of a sample, where a first beam of light at a first wavelength and having a first energy is directed at the sample for a first length of time. A combination of the first wavelength, the first energy, and the first length of time is sufficient to cause temporary damage to the sample. The damage includes at least one of atomic changes and molecular changes to the sample. The first beam of light is reflected from the sample to create a first reflected beam having properties indicative of the properties of the sample. The properties of the first reflected beam are sensed to create a first electrical signal indicative of the properties of the sample.

A length of time is waited, sufficient for the temporary damage to the sample to substantially heal, before a second beam of light at a second wavelength and having a second energy is directed at the sample for a second length of time. A combination of the second wavelength, the second energy, and the second length of time is sufficient to cause temporary damage to the sample, where the damage includes at least one of atomic changes and molecular changes to the sample. The second beam of light is reflected from the sample to create a second reflected beam having properties indicative of the properties of the sample. The properties of the second reflected beam are sensed to create a second electrical signal indicative of the properties of the sample. The first and second electrical signals are analyzed to determine the properties of the sample.

In this manner, the temporary damage that is imparted to the sample is allowed to heal before additional irradiation is directed at the sample. Thus, multiple scans can be performed, but the readings from the scans do not exhibit the drift that typically accompanies such serialized scans, because the damage is allowed to heal before subsequent scans are preformed.

In various preferred embodiments, the first wavelength is equal to the second wavelength, the first energy is equal to the second energy, and the first length of time is equal to the second length of time. In some embodiments the first wavelength and the second wavelength are both at least one of deep ultraviolet and vacuum ultraviolet. In some embodiments, during the length of time sufficient for the temporary damage to the sample to substantially heal, the sample is not irradiated.

In some embodiments, during the length of time sufficient for the temporary damage to the sample to substantially heal, a third beam of light at a third wavelength and having a third energy is directed at the sample for a third length of time, where a combination of the third wavelength, the third energy, and the third length of time is insufficient to either cause damage to the sample or to substantially impede the healing of the temporary damage to the sample. The third beam of light is reflected from the sample to create a third reflected beam having properties indicative of the properties of the sample. The properties of the third reflected beam are sensed to create a third electrical signal indicative of the properties of the sample. The first, second, and third electrical signals are analyzed to determine the properties of the sample. In some embodiments the third wavelength is at least one of visible light and infrared light. In some embodiments the method is performed by one of an ellipsometer and a reflectometer.

According to another aspect of the invention there is described an instrument for performing a measurement of properties of a sample. The instrument includes a first beam source for directing a first beam of light at a first wavelength and having a first energy at the sample for a first length of time, where a combination of the first wavelength, the first energy, and the first length of time is sufficient to cause temporary damage to the sample, the damage including at least one of atomic changes and molecular changes to the sample. A stage holds the sample, the sample thereby reflecting the first beam of light to create a first reflected beam having properties indicative of the properties of the sample. A first sensor senses the properties of the first reflected beam to create a first electrical signal indicative of the properties of the sample. Means are provided for waiting a length of time sufficient for the temporary damage to the sample to substantially heal.

A second beam source directs a second beam of light at a second wavelength and at a second energy at the sample for a second length of time, where a combination of the second wavelength, the second energy, and the second length of time is sufficient to cause temporary damage to the sample, the damage including at least one of atomic changes and molecular changes to the sample. The stage holds the sample, the sample thereby reflecting the second beam of light to create a second reflected beam having properties indicative of the properties of the sample. A second sensor senses the properties of the second reflected beam to create a second electrical signal indicative of the properties of the sample. An analyzer analyzes the first and second electrical signals to determine the properties of the sample.

In some embodiments the first sensor and the second sensor are a single sensor. In some embodiments the instrument is one of an ellipsometer and a reflectometer.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

When a combined measurement is required, the system is driven in such a way that signals using different lamps are being collected alternately, e.g. by alternately collecting visible and vacuum ultraviolet signals. This is known as interleave. The result of this method is to avoid performance degradation. This degradation has an increasing magnitude with increasing exposure time to such wavelengths, but in general they are not permanently destructive, so the initial condition of the sample is recovered after some time if no other physical or environmental conditions change.

One embodiment of the method relies on exposing measurement samples to vacuum ultraviolet light for the lowest possible amount of time, and to repeat exposure after a delay in order to achieve the integration time requested by the number of scans. This method takes advantage of a phenomenon reversibility based on time delay. In some embodiments the required time delay is granted by exposure to visible light, which doesn't affect the sample under analysis. In this way the total amount of time needed for measurement purposes doesn't change and the only change is in the measurement sequence. Preliminary results show an improvement factor of between about two and about four in system performances such as precision.

Figure 1:
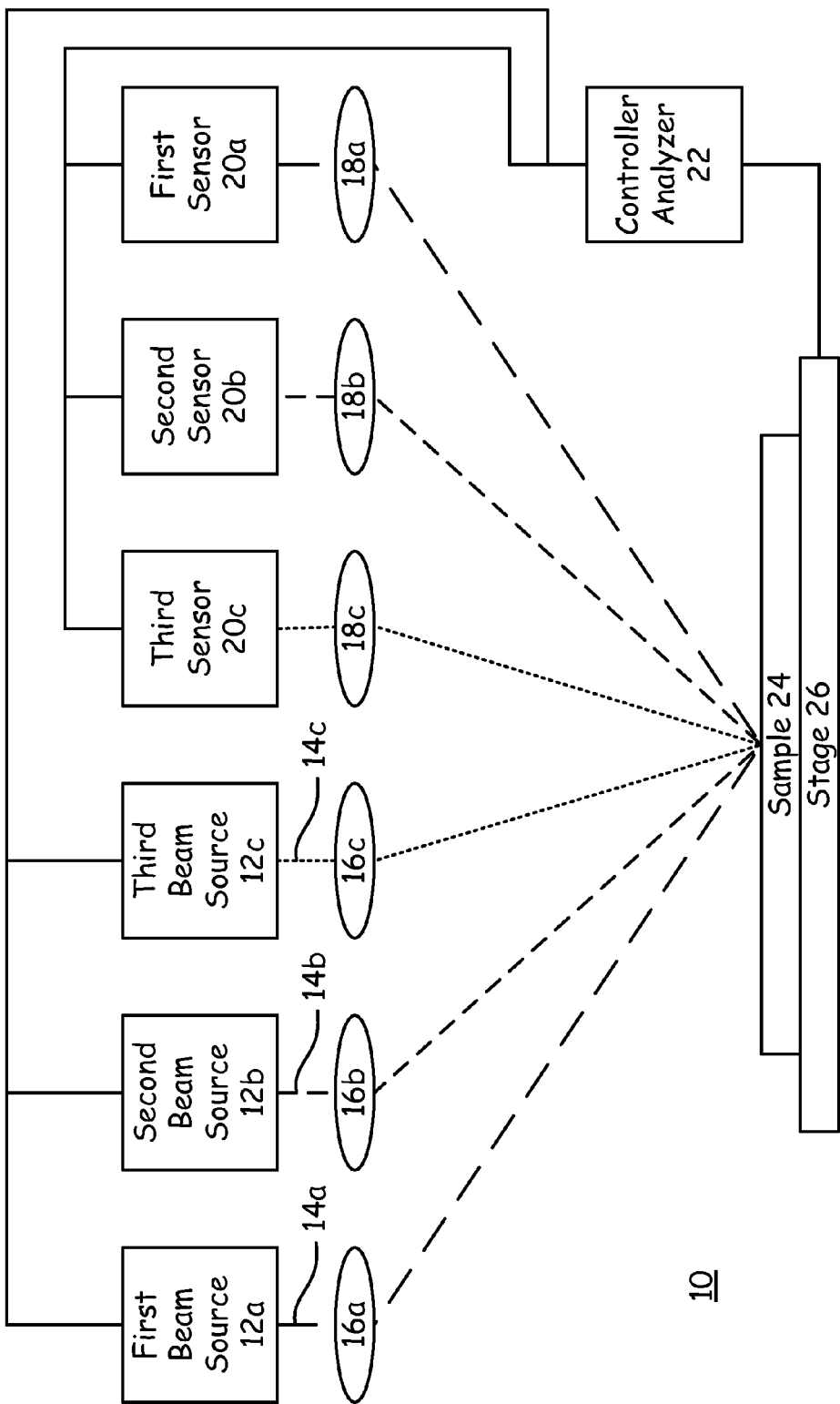
FIG. 1 is a functional block diagram of a system according to a first embodiment of the present invention.

With reference now to FIG. 1, there is depicted a system 10 according to a first embodiment of the present invention. The system 10 has first, second, and third beam sources 12a, 12b, and 12c, respectively producing light beams 14a, 14b, and 14c. In the embodiment depicted in FIG. 1, separate (at least in part) optical paths 16a, 16b, and 16c, direct the light beams 14 toward a sample 24. The light beams 14 are reflected off of the sample 24 and back into separate (at least in part) optical paths 18a, 18b, and 18c. The light beams 14a, 14b, and 14c are then respectively sensed by first sensor 20a, second sensor 20b, and third sensor 20c.

Figure 2:
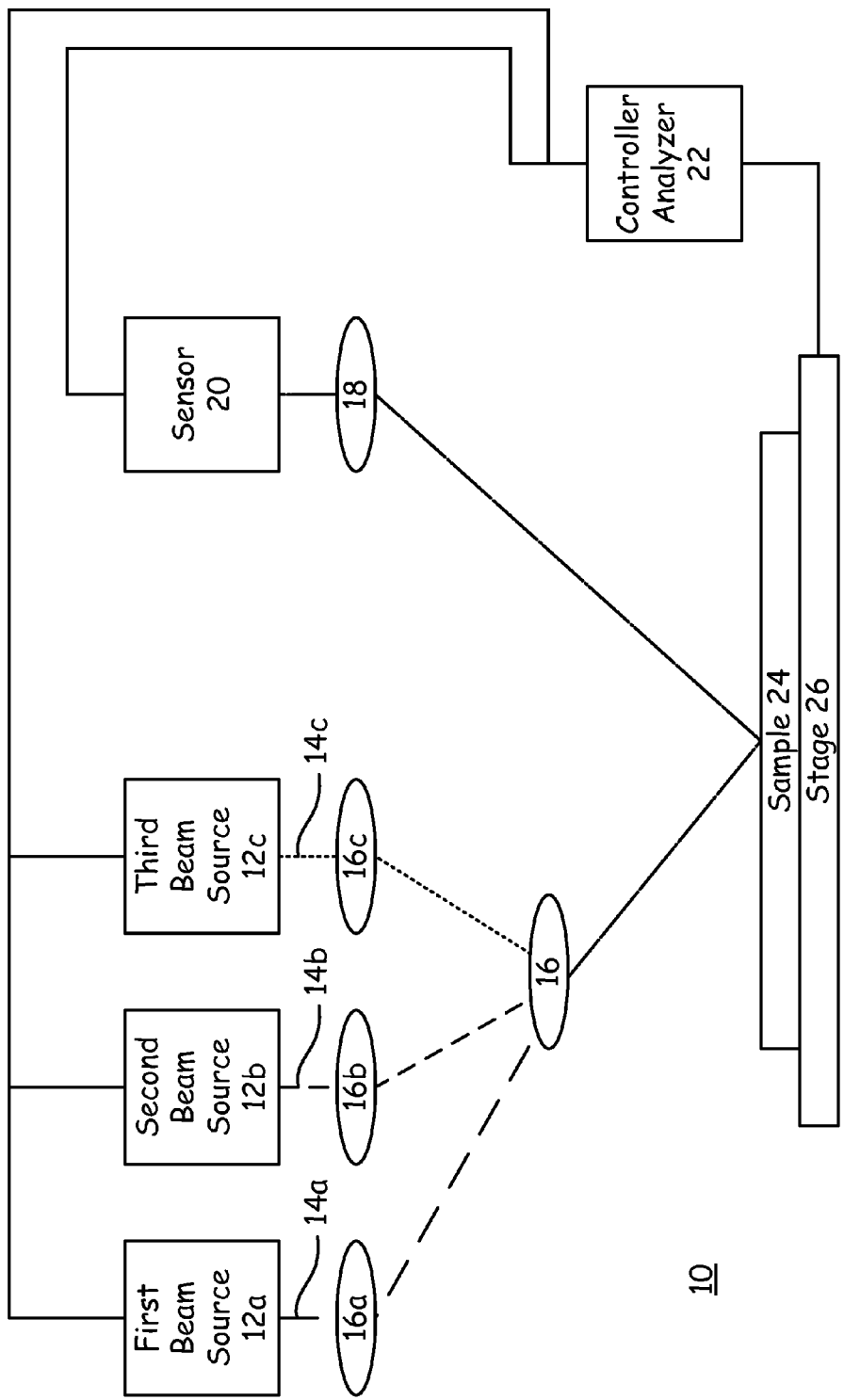
FIG. 2 is a functional block diagram of a system according to a second embodiment of the present invention.

In the embodiment depicted in FIG. 2, the optical paths 16 and 18 are combined (at least in part) for the three beams 14a, 14b, and 14c. Also in the embodiment depicted in FIG. 2, there is a single sensor 20 that receives the reflected beams 14 from the sample 24. Combinations of the elements of FIGS. 1 and 2 are also contemplated hereby.

A combination controller and analyzer unit 22 both controls the operation of the beam sources 12 and receives electrical signals from the sensors 20. The controller and analyzer unit 22 also controls the movement of the stage 26. In this manner, readings can be taken from any portion of the sample 24 as desired. The functions of the controller and analyzer unit 22 could also be split out into two or more separate units, having the functions as generally described herein.

In one example of the operation of the system 10, the first beam source 12a is a deep ultra violet source, the beam 14a from which can damage the sample 24 when the energy and duration of the beam are sufficiently long. The first beam source 12a is instructed by the controller 22 to deliver a beam 14a at the wavelength of the beam source 12a, and for a time and an energy whereby damage is imparted to the sample 24, but such that the sample 24 is not permanently damaged. As the beam 14a irradiates the sample 24, the first sensor 20a collects the reflected beam, and sends signals back to the analyzer 22. The controller 22 then stops the first beam 14a, and the controller 22 allows the sample 24 to heal from the damage, by not irradiating the sample 24 with any beam 14 that would impart further damage to the sample 24, or otherwise unduly impair the healing process of the sample 24.

This could be accomplished by not irradiating the sample 24 with any beam 14 whatsoever, or irradiating the sample 24 with a beam 14 that exhibits at least one of a wavelength, duration, or energy that is insufficient for the beam 14 to further damage or substantially interfere with the healing of the sample 24. This interruption of the beam 14 during the healing period could be produced by physically extinguishing the relevant beam sources 12, or by the use of shutters that block one or more of the beams 14, light absorbing gases that are introduced somewhere between the beam sources 12 and the sample 24, de-focusing the optics 16, or other such methods.

It is appreciated that there tends to be at least some correlation between the wavelength, duration, and energy of the beam 14, the amount of damage imparted to the sample 24, and the length of healing time required by the sample 24. Thus, these variables could be adjusted, such as by programming the controller 22, so that beams 14 of either relatively longer duration or relatively shorter duration could be produced, and then healing times of either relatively longer duration or relatively shorter duration would be required. These variables could be balanced in manner such that the healing time between such damaging irradiations could either be minimized, or productively used, such as in the manner as described hereinafter.

Once the healing is substantially complete, then another of the beam sources 12 is fired. It could be the same beam source 12a, or one of the other beam sources 12b and 12c. An additional number of beam sources 12 could also be provided and used. In one embodiment, the second beam source 12b is fired, producing a vacuum ultra violet light beam 14b, at an energy and for a duration that is sufficient to damage the sample 24. As the beam 14b irradiates the sample 24, the second sensor 20b collects the reflected beam, and sends signals back to the analyzer 22. The beam 14b is stopped before the damage is permanent, and again the sample 24 is allowed to heal.

The signals gathered by the analyzer 22 from the sensors 20 during the firing of the beam sources 20 are analyzed to determine the desired characteristics of the sample 24. In so doing, the trending effects caused by the damage that is imparted to the sample 24 does not significantly effect the sensed characteristics, because the sample 24 is preferably always given an opportunity to heal between damaging irradiations. Thus, the system 10 can be used for both scanning and interleaving, as described above.

In one embodiment, the third beam source 12c produces a beam 14c that is not damaging to the sample 24, such as visible light, and yet which is able to determine desired characteristics of the sample 24. Further, the beam 14c produced also does not substantially inhibit the healing process of the sample 24. Therefore, in some embodiments, the third beam source 12c is used to irradiate the sample 24 during the healing periods, and the reflected beam is sensed by the third sensor 20c, and the analyzer 22 collects and computes information about the sample 24 based at least in part on the characteristics of the reflected third beam 14c. Thus, in these embodiments, the healing time for the sample 24 is not just idle time on the system 10, but instead is put to a productive use.

The methods and operation of the system 10 as described above can be implemented in an ellipsometer or a reflectometer, which then computes properties of the sample 24 as known in the art.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of performing a measurement of properties of a sample, the method comprising the steps of:
   directing a first beam of light at a first wavelength and having a first energy at the sample for a first length of time, where a combination of the first wavelength, the first energy, and the first length of time is sufficient to cause temporary damage to the sample, the damage including at least one of atomic changes and molecular changes to the sample,
   reflecting the first beam of light from the sample to create a first reflected beam having properties indicative of the properties of the sample,
   sensing the properties of the first reflected beam to create a first electrical signal indicative of the properties of the sample,
   waiting a length of time sufficient for the temporary damage to the sample to substantially heal,
   directing a second beam of light at a second wavelength and having a second energy at the sample for a second length of time, where a combination of the second wavelength, the second energy, and the second length of time is sufficient to cause temporary damage to the sample, the damage including at least one of atomic changes and molecular changes to the sample,
   reflecting the second beam of light from the sample to create a second reflected beam having properties indicative of the properties of the sample,
   sensing the properties of the second reflected beam to create a second electrical signal indicative of the properties of the sample, and
   analyzing the first and second electrical signals to determine the properties of the sample.

2. The method of claim 1, wherein the first wavelength is equal to the second wavelength.

3. The method of claim 1, wherein the first energy is equal to the second energy.

4. The method of claim 1, wherein the first length of time is equal to the second length of time.

5. The method of claim 1, wherein the first wavelength is equal to the second wavelength, the first energy is equal to the second energy, and the first length of time is equal to the second length of time.

6. The method of claim 1, wherein the first wavelength and the second wavelength are both at least one of deep ultraviolet and vacuum ultraviolet.

7. The method of claim 1, wherein during the length of time sufficient for the temporary damage to the sample to substantially heal, the sample is not irradiated.

8. The method of claim 1, further comprising:
   during the length of time sufficient for the a temporary damage to the sample to substantially heal, a third beam of light at a third wavelength and having a third energy is directed at the sample for a third length of time, where a combination of the third wavelength, the third energy, and the third length of time is insufficient to either cause damage to the sample or to substantially impede the healing of the a temporary damage to the sample,
   reflecting the third beam of light from the sample to create a third reflected beam having properties indicative of the properties of the sample, sensing the properties of the third reflected beam to create a third electrical signal indicative of the properties of the sample, and analyzing the first, second, and third electrical signals to determine the properties of the sample.

9. The method of claim 1, wherein the third wavelength is at least one of visible light and infrared light.

10. The method of claim 1, wherein the method is performed by one of an ellipsometer and a reflectometer.

11. An instrument for performing a measurement of properties of a sample, the instrument comprising:
  a first beam source for directing a first beam of light at a first wavelength and having a first energy at the sample for a first length of time, where a combination of the first wavelength, the first energy, and the first length of time is sufficient to cause a temporary damage to the sample, the damage including at least one of atomic changes and molecular changes to the sample,
  a stage for holding the sample, the sample thereby reflecting the first beam of light to create a first reflected beam having properties indicative of the properties of the sample,
  a first sensor for sensing the properties of the first reflected beam to create a first electrical signal indicative of the properties of the sample,
  means for waiting a length of time sufficient for the a temporary damage to the sample to substantially heal,
  a second beam source for directing a second beam of light at a second wavelength and having a second energy at the sample for a second length of time, where a combination of the second wavelength, the second energy, and the second length of time is sufficient to cause a temporary damage to the sample, the damage including at least one of atomic changes and molecular changes to the sample,
  the stage for holding the sample, the sample thereby reflecting the second beam of light to create a second reflected beam having properties indicative of the properties of the sample,
  a second sensor for sensing the properties of the second reflected beam to create a second electrical signal indicative of the properties of the sample, and
  an analyzer for analyzing the first and second electrical signals to determine the properties of the sample.

12. The instrument of claim 11, wherein the first wavelength is equal to the second wavelength, the first energy is equal to the second energy, and the first length of time is equal to the second length of time.

13. The instrument of claim 11, wherein the first beam source and the second beam source are a single beam source.

14. The instrument of claim 11, wherein the first sensor and the second sensor are a single sensor.

15. The instrument of claim 11, wherein the first wavelength and the second wavelength are both at least one of deep ultraviolet and vacuum ultraviolet.

16. The instrument of claim 11, wherein during the length of time sufficient for the a temporary damage to the sample to substantially heal, the sample is not irradiated.

17. The instrument of claim 11, further comprising:
  a third beam source for directing a third beam of light at a third wavelength and having a third energy is directed at the sample for a third length of time, where a combination of the third wavelength, the third energy, and the third length of time is insufficient to either cause damage to the sample or to substantially impede the healing of the a temporary damage to the sample, the third beam of light directed at the sample during the length of time sufficient for the a temporary damage to the sample to substantially heal,
  the stage for holding the sample, the sample thereby reflecting the third beam of light to create a third reflected beam having properties indicative of the properties of the sample,
  a third sensor for sensing the properties of the third reflected beam to create a third electrical signal indicative of the properties of the sample, and
  the analyzer for analyzing the first, second, and third electrical signals to determine the properties of the sample.

18. The instrument of claim 17, wherein the third wavelength is at least one of visible light and infrared light.

19. The instrument of claim 17, wherein the first sensor, the second sensor, and the third sensor are a single sensor.

20. The instrument of claim 11, wherein the instrument is one of an ellipsometer and a reflectometer.

* * * * *